United States Patent [19]
Kehat

[11] Patent Number: 6,021,960
[45] Date of Patent: Feb. 8, 2000

[54] COLORED LIGHT SHOWER HEAD

[76] Inventor: Joel Kehat, P.O. Box 707, Ramat Ishay 30095, Israel

[21] Appl. No.: 08/949,598

[22] Filed: Oct. 14, 1997

[30] Foreign Application Priority Data

Oct. 15, 1996 [IL] Israel ........................................ 119431

[51] Int. Cl.[7] .................................................. B05B 15/00
[52] U.S. Cl. ............................. 239/289; 239/18; 362/96
[58] Field of Search ............................ 239/289, 18, 19, 239/20; 362/192, 96, 54

[56] References Cited

U.S. PATENT DOCUMENTS

| | | | |
|---|---|---|---|
| 2,629,516 | 2/1953 | Badham | 362/112 |
| 3,845,291 | 10/1974 | Portyrata | 240/26 |
| 4,564,889 | 1/1986 | Bolson | 362/192 |
| 4,616,298 | 10/1986 | Bolson | 362/192 |
| 5,207,499 | 5/1993 | Vajda et al. | 362/96 |
| 5,539,624 | 7/1996 | Dougherty | 362/32 |
| 5,552,973 | 9/1996 | Hsu | 362/192 |
| 5,823,431 | 10/1998 | Pierce | 239/19 |

*Primary Examiner*—Kevin Shaver
*Assistant Examiner*—David Deal
*Attorney, Agent, or Firm*—Frishauf, Holtz, Goodman, Langer & Chick, P.C.

[57] ABSTRACT

A shower for chrome-hydro-therapy includes a shower head adapted to issue a spray of colored water onto the body of a person. The shower head includes a rear portion provided with a connector to the domestic water supply and an open front portion covered by a screen or perforated member adapted to eject the water in a finely divided spray. The shower head contains a colored light source mounted in concentric alignment with the screen or perforated member, so as to direct colored light rays into the spray. In a first embodiment, the light source is in the form of a lamp comprising a bulb and at least one battery which is enclosed in a waterproof, transparent housing. In another embodiment, the light is emitted from the end of an optical fiber which has its other end optically connected to a colored light source outside the shower. In both embodiments, the light can be switched on or off by the user.

13 Claims, 6 Drawing Sheets

6,021,960

COLORED LIGHT SHOWER HEAD

The invention relates to a shower head configured to emit a spray of water colored by an integral light source.

BACKGROUND OF THE INVENTION

Color-therapy—or chromo-therapy—and hydrotherapy are two healing methods which have been practiced from ancient times and which today are gaining more and more acceptance with ever widening fields of application.

Treatment of many diseases by application of colored light is being practiced in today's alternative medicine and is being gradually accepted by modern medicine, especially in psychotherapy. Each specific color is considered to have a particular quality effecting certain energy centers in the human body, linked to body physiology. Stimulation of these energy centers by means of a particular color is apt to modify physiological processes and thereby to heal certain diseases.

Hydrotherapy, the external application of a stream of water, is being used by specialists in physical medicine and rehabilitation and by physical therapists in the treatment of diseases and injuries. The primary value of water in the therapy is a medium for application and reduction of temperature or other forms of energy or stimuli and/or a massaging agent.

The selective use of color in the treatment of human diseases is a complex healing art. Color may be applied alone or in special therapeutic combinations to enhance the potential of color healing through synergistic effects. The methods by which the frequencies of color can be transmitted are numerous, such as using sunlight or artificial light passed through color filters of various hues, or naturally colored lamps.

SUMMARY OF THE INVENTION

In view of the advantages of both chromo-therapy and hydro-therapy, it is the main object of the present invention to combine both methods and to provide means serving to treat a person by means of a water shower which can be colored in any hue suitable for treatment of the specific disease.

It is another object to provide means of the above kind which can be easily applied and permit changing of water temperature and color without effort.

Still another object is to provide means for hydro-chromo-therapy which present no danger, neither to the patient nor to the medical personnel, and which should be available at low cost so as to permit its use not only in medical installations, but in any home.

The invention relates to a shower head, both stationary or hand held, which includes a rear portion provided with a connector to a supply of hot and cold water and a front portion attachable the rear portion by, for example, screw thread and which contains a perforated screen configured to eject the water in spray form. According to the present invention the shower head contains a colored light source mounted substantially in the center of the shower head and co-ordinated with the direction of the water stream. The light source is insulated against penetration of water and may be in the form of a colored bulb or, preferably, in the form of an incandescent bulb and an exchangeable color filter mounted in front of the bulb.

The light source is in the form of an electric low-voltage lamp in the form of a substantially waterproof cylindrical housing. It includes a light bulb extending towards the front and is supplied current from one or more electric cells (batteries) enclosed in the housing and energized by means of an on/off switch in its rear end which protrudes out of the rear end of the shower head.

In a first embodiment of the shower head the lamp is enclosed in a cylindrical casing which is integral with the rear portion and is closed by a transparent front cover, while having an open rear end for insertion of the lamp. In this embodiment the bulb is colored and may be exchanged by a bulb of a different color. It is understood that in this embodiment the light passes through the perforations in the front sreen member and colors the water passing therethrough as well.

In a second embodiment the bulb is enclosed in a waterproof transparent envelope in the front of the housing. The lamp is mounted in a tubular lamp holder concentric with the rear portion of the shower and extends through a central opening in the front screen member, with the bulb in its envelope surrouded by an annular water spray. In this embodiment the bulb may be exchanged for a bulb of a different color or it may be uncolored with an exchangeable colored filter mounted onto the front of the envelope.

DETAILED DESCRIPTION OF THE DRAWINGS

Figure 1:
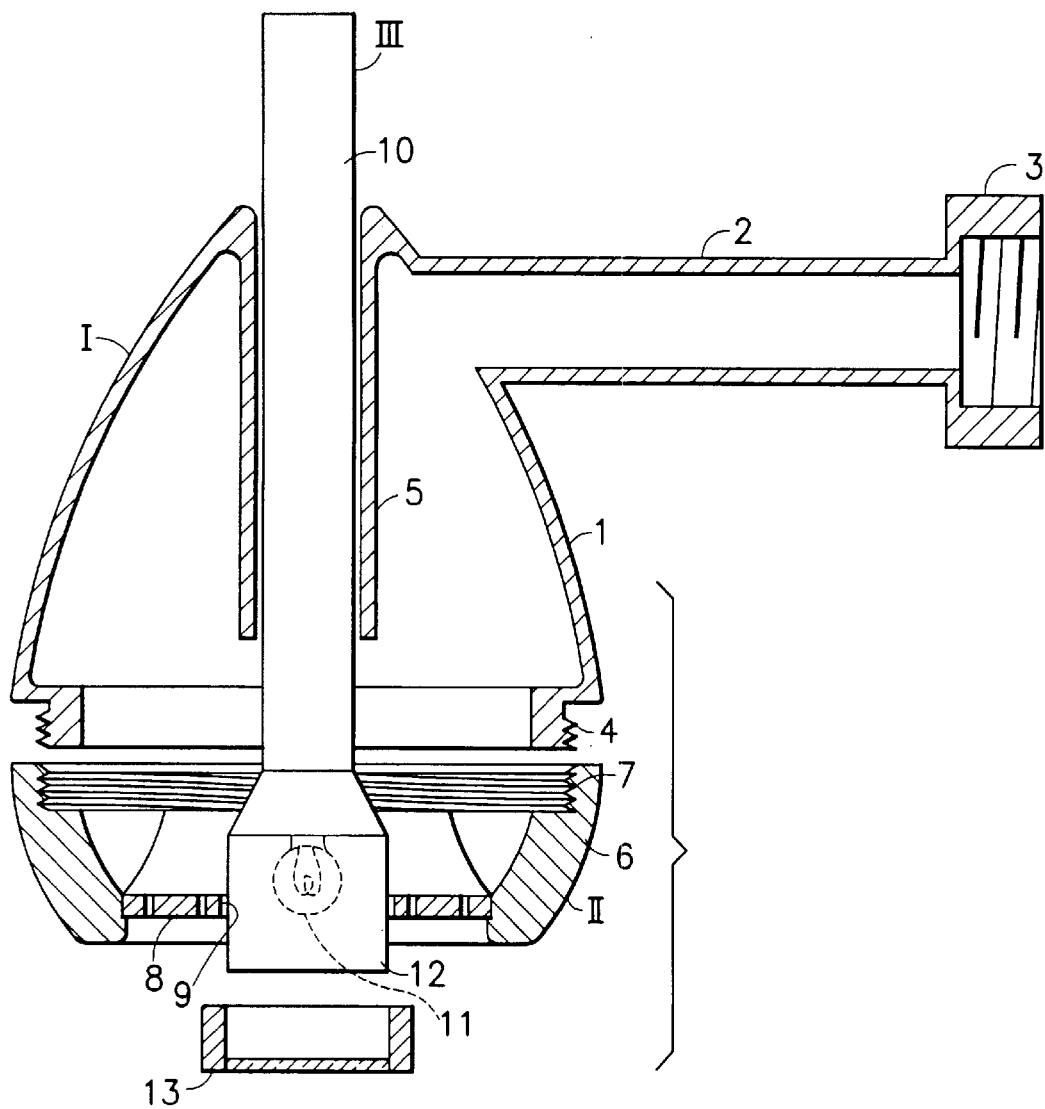
FIG. 1 is a sectional view of a stationary shower head having a colored light source protruding out of its front portion.
Figure 2:
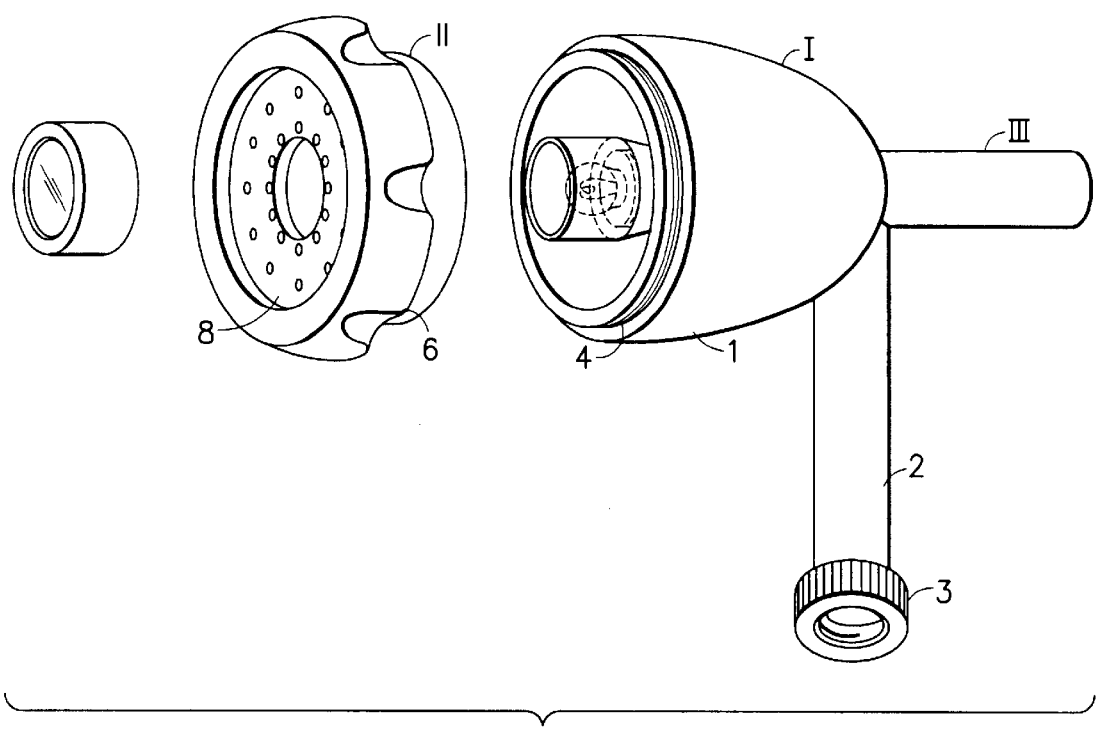
FIG. 2 is an isometric view of the shower head of FIG. 2, with the components in disassembled state.

The shower head illustrated in FIGS. 1 and 2 includes a rear portion I in the shape of a half-ellipsoid 1 and is connected to a domestic water supply by a pipe 2 terminating in a screw-connector 3. Its open front is screw-threaded 4 for connection of the front portion II. The rear end is open and is continued in frontal direction by a tubular lamp holder 5 which extends close to the front end of the half-ellipsoid. The front portion II is in the shape of a flat cap 6 provided with internal screw thread 7 corresponding to the screw thread on the rear portion and has its front covered by an annular screem 8 (perforating member) creating the shower spray. The center of the screen is open (9) to permit the lamp III to protrude through it to the front. The lamp III contains a waterproof housing 10 which contains one or more electric cells (batteries) 25 (see FIGS. 5 and 6) and a bulb 11 enclosed in a waterproof transparent envelope 12. The lamp is mounted in the lamp holder 5 with its rear end and switch protruding out of the rear portion and with the transparent envelope slightly protruding beyond the screen 8. A cap-shaped colored filter 13 is configured to be mounted on the envelope and to color the water drops ejected through the screen perforations.

Figure 3:
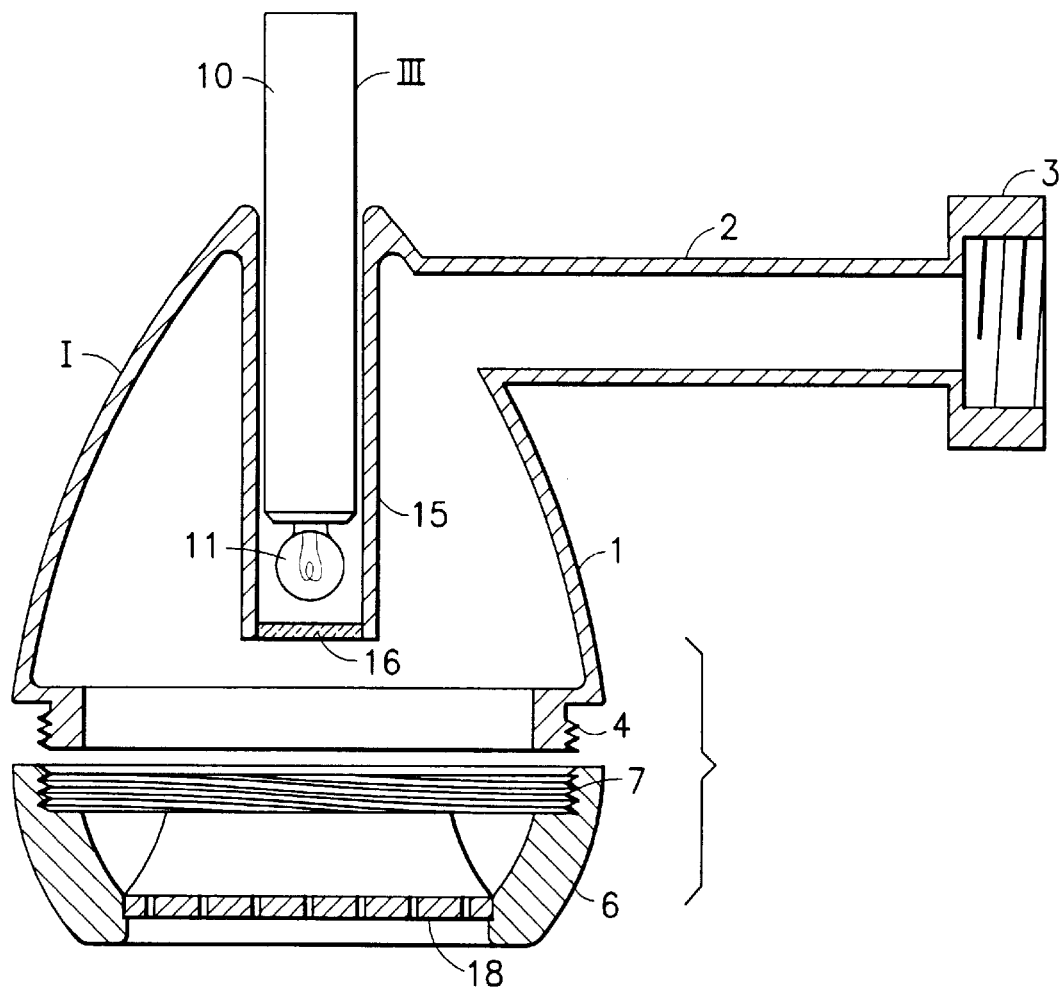
FIG. 3 is a sectional view of a stationary shower head having a colored light source mounted in its rear portion.
Figure 4:
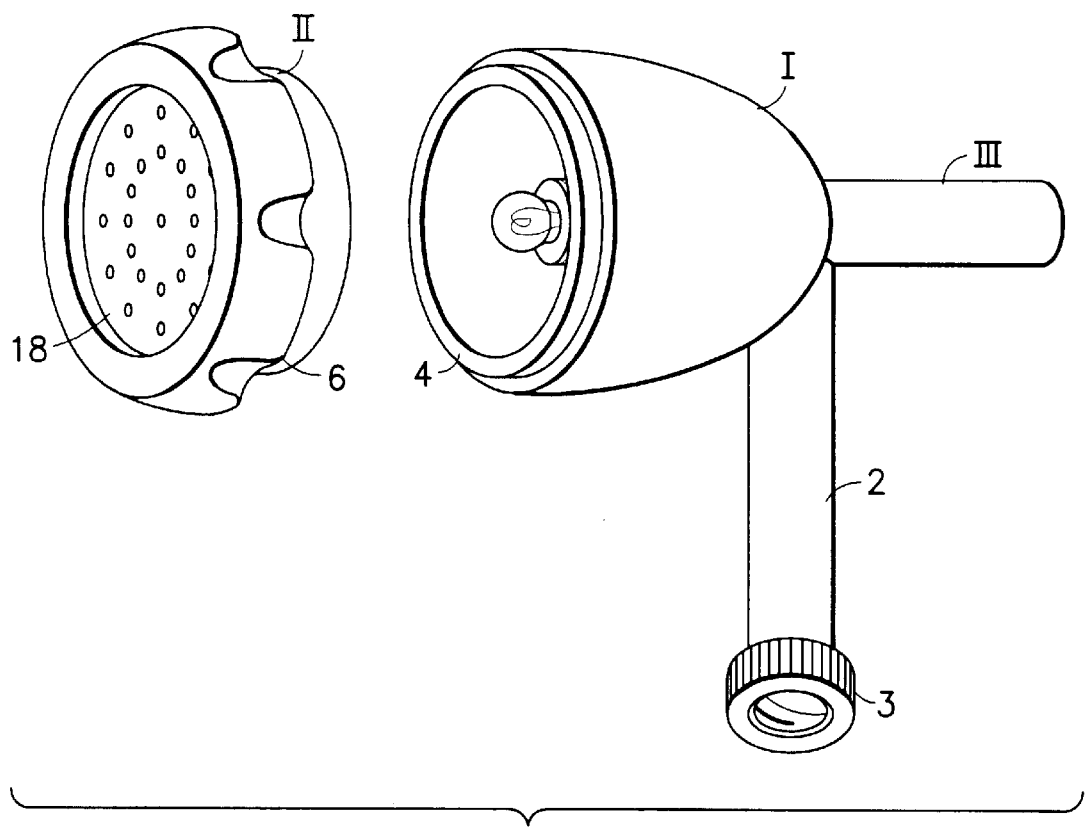
FIG. 4 is an isometric view of the shower head of FIG. 3 with the components in disassembled state.

FIGS. 3 and 4 illustrate the same shower head as that shown in FIGS. 1 and 2, but with a different arrangement of the light source. In these figures the same numerals are being used to indicate identical components and these are not going to be desribed specifically. As shown in FIG. 3, the lamp III, comprising a waterproof housing 10 and a bulb 11, is located in a casing 15 which is closed at its front end by a transparent end cover 16. The casing 15 is mounted in the rear portion 1 of the shower head I concentric therewith and has an open rear end for insertion of the lamp. The screen 8 (perforated member) is circular and it becomes evident that the colored light passes through the screen perforations together with the water particles which become colored as well.

As an alternative the screen may be made of a transparent, colored material which will transmit its color to the water passing therethrough.

Figure 5:
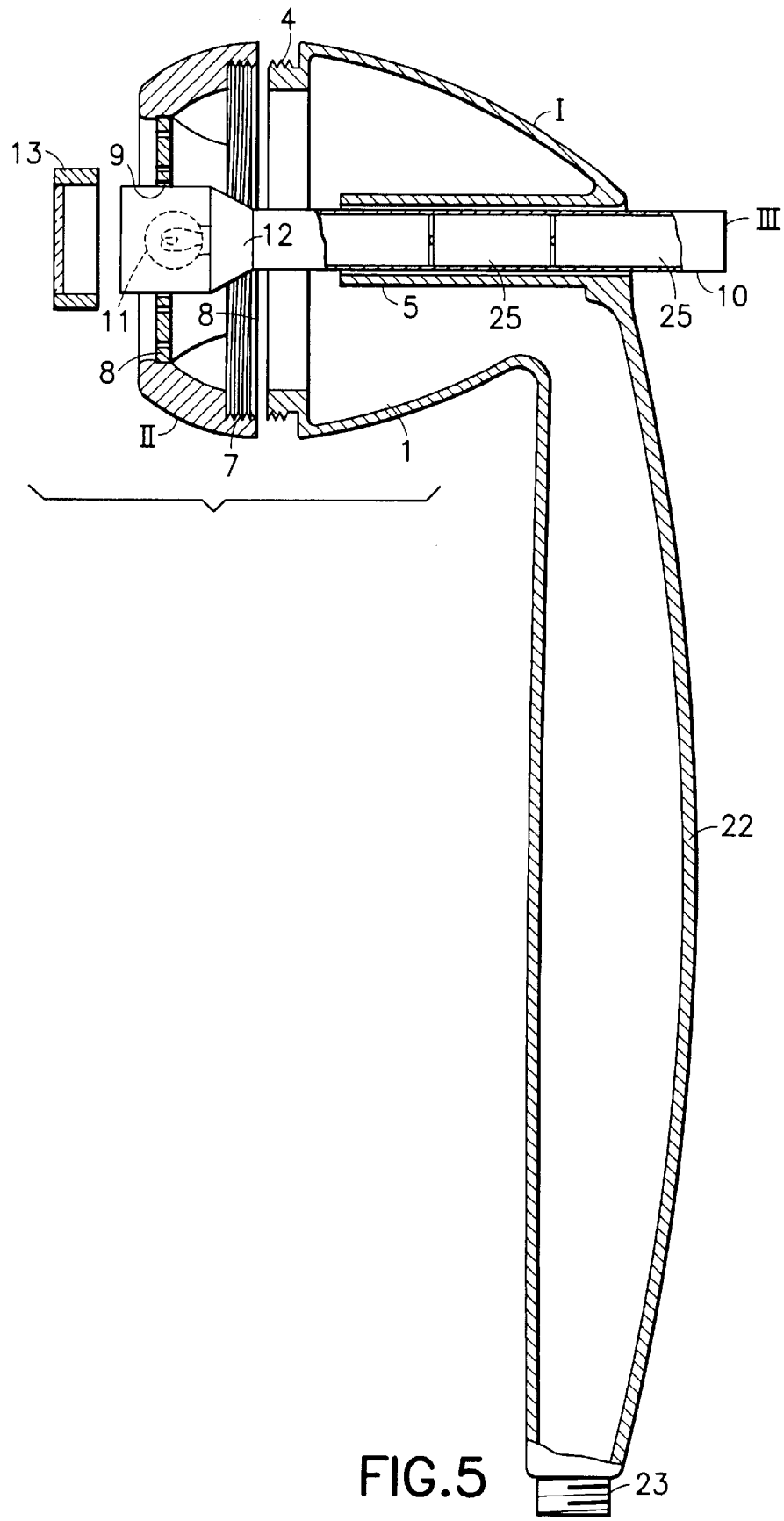
FIG. 5 is a sectional view of a hand-held shower head similar to that illustrated in FIG. 1.
Figure 6:
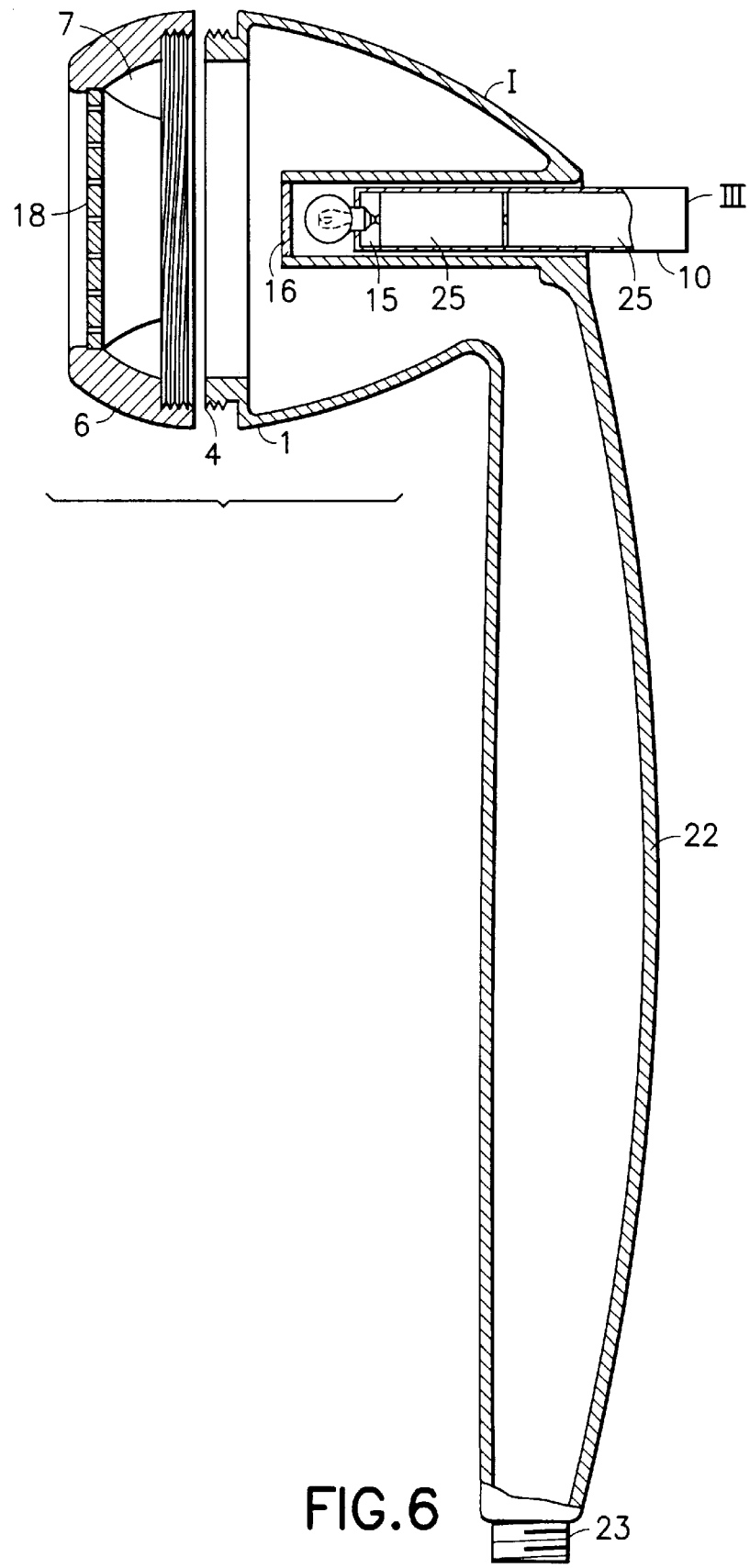
FIG. 6 is a sectional view of a hand-held shower head similar to that illustrated in FIG. 3.

The shower heads illustrated in FIGS. 5 and 6 are identical with those illustrated in FIGS. 1 and 3 respectively, with the difference that they are hand-held and that the connecting pipe 2 is replaced by a handle 22 terminating in a screw connection 23. The heads themselves and the installation of the lamp is the same, and will not be described again.

The light source is preferably an incandescent bulb energized by eletric cells (batteries) 25, which may be primary or rechargeable, but it is proposed to use other light sources, such as a Light Emitting Diode (LED) instead together with the provision of a suitable voltage source. Another way of producing colored water spray is by placing the open end of a light-conducting fiber, a so-called optical fiber, into the center of the shower head, while the other end of the fiber is optically connected to a light source positioned outside the shower bath. In this way no electric insulating means become necessary.

The two methods of mounting the light source in the shower head illustrated in the foregoing are arbitrary and may be changed with the construction of the head itself, as long as the colored light rays extend in the direction of the water spray and color the water drops.

I claim:

1. A shower head for chrome-hydro-therapy adapted to issue a spray of colored water on the body of a person, comprising;

a shower head having a rear portion to be connected to a domestic supply of hot and cold water, and a front portion including a perforated member adapted to eject a water stream in the form of finely divided drops, to thereby form a water spray; and a colored light source supplied with electrical current from at least one battery, said colored light source being mounted in said shower head in waterproof fashion to prevent water from entering into the colored light source, and said colored light source being arranged to direct colored light rays only in a frontal direction into said water spray such that the colored light rays extend in the direction of the water spray to color the water drops in the water spray.

2. The shower head of claim 1, wherein said colored light source comprises a lamp having a waterproof cylindrical housing containing said at least one battery and a light bulb in a front end thereof, said lamp being mounted in said shower head in substantially concentric alignment with said perforated member and substantially perpendicular to said perforated member.

3. The shower head of claim 2, wherein said lamp is secured in a tubular lamp holder which is integral with said rear portion of said shower head, in substantially concentric and perpendicular alignment with said perforated member, said lamp holder having an open rear end for insertion of said lamp.

4. The shower head of claim 3, wherein said lamp is provided with an on/off switch at a rear end portion thereof which protrudes out of the open rear end of said lamp holder.

5. The shower head of claim 3, wherein said tubular lamp holder has a closed front end which is closed by a transparent cover, and wherein said light bulb is colored.

6. The shower head of claim 5, wherein said perforated member is made of a transparent colored material so as to color the water drops in the water spray.

7. The shower head of claim 3, wherein said tubular lamp holder is open at both ends, and wherein said lamp protrudes out of the open front end of said lamp holder and through a central hole in said perforated member.

8. The shower head of claim 7, wherein said light bulb of said lamp is enclosed in a transparent envelope which extends through a substantially central hole in said perforated member.

9. The shower head of claim 8, wherein an exchangeable colored filter is mounted on the front end of said transparent envelope enclosing said lamp.

10. The shower head of claim 1, wherein said light source comprises a light emitting diode supplied with electric current from said battery.

11. The shower head of claim 1, wherein said battery is a primary cell.

12. The shower head of claim 1, wherein said battery is a rechargeable cell.

13. A shower head for chrome-hydro-therapy adapted to issue a spray of colored water on the body of a person, comprising:

a shower head having a rear portion to be connected to a domestic supply of hot and cold water, and a front portion including a perforated member adapted to eject a water stream in the form of finely divided drops, to thereby form a water spray; and a colored light source positioned remote from said shower head and connected to a first end of a light-conducting optical fiber, said light-conducting optical fiber having a second end mounted in said shower head in substantially concentric alignment with the direction of said water spray issuing from said shower head so as to emit colored light rays which extend in the direction of the water spray to color the water drops in the water spray.

* * * * *